United States Patent
Warner et al.

(10) Patent No.: US 11,395,597 B2
(45) Date of Patent: Jul. 26, 2022

(54) SYSTEM AND METHOD FOR EVALUATING BLOOD FLOW IN A VESSEL

(71) Applicant: General Electric Company, Schenectady, NY (US)

(72) Inventors: Adrian F. Warner, Delafield, WI (US); Daniel R. Schneidewend, Menomonee Falls, WI (US); Daniel J. Nowicki, Cedarburg, WI (US); Joel Q. Xue, Brown Deer, WI (US)

(73) Assignee: General Electric Company, Schenectady, NY (US)

( * ) Notice: Subject to any disclaimer, the term of this patent is extended or adjusted under 35 U.S.C. 154(b) by 332 days.

(21) Appl. No.: 16/019,229

(22) Filed: Jun. 26, 2018

(65) Prior Publication Data

US 2019/0387981 A1    Dec. 26, 2019

(51) Int. Cl.
| | |
|---|---|
| *A61B 5/0215* | (2006.01) |
| *A61B 5/026* | (2006.01) |
| *A61B 5/00* | (2006.01) |
| *A61M 25/00* | (2006.01) |

(52) U.S. Cl.
CPC ............ *A61B 5/0215* (2013.01); *A61B 5/026* (2013.01); *A61B 5/6852* (2013.01); *A61M 2025/0002* (2013.01)

(58) Field of Classification Search
None
See application file for complete search history.

(56) References Cited

U.S. PATENT DOCUMENTS

| | | | |
|---|---|---|---|
| 2004/0055993 A1 | 3/2004 | Moudgil et al. | |
| 2004/0147847 A1* | 7/2004 | Ng | A61B 5/022 600/485 |
| 2004/0186524 A1* | 9/2004 | Chinchoy | A61B 5/0215 607/17 |
| 2007/0066888 A1* | 3/2007 | Maschke | A61B 8/12 600/424 |

(Continued)

FOREIGN PATENT DOCUMENTS

| | | |
|---|---|---|
| CN | 104217418 | 12/2014 |
| EP | 2916735 | 9/2019 |

(Continued)

*Primary Examiner* — Alex M Valvis
*Assistant Examiner* — Aurelie H Tu

(57) ABSTRACT

A system for evaluating blood flow in a vessel of a patient includes a catheter containing a first pressure sensor and a second pressure sensor and configured to simultaneously measure pressure data within a vessel on either side of a stenosis. Pressure data generated by the catheter includes a first series of pressure measurements from the first pressure sensor a second series of pressure measurements from the second pressure sensor. The system further includes an FFR calculation module executable on one or more processors and configured to calculate a stability index for each of two or more portions of the pressure data, wherein each stability index indicates at least one of heart rate stability and catheter stability for the respective portion of the pressure data. An optimal time window is identified based on the stability indexes for calculation of fractional flow reserve (FFR) based on the pressure data. An FFR value is then calculated based on the pressure data in the optimal time window.

22 Claims, 5 Drawing Sheets

(56) References Cited

U.S. PATENT DOCUMENTS

| | | |
|---|---|---|
| 2009/0082678 A1 | 3/2009 | Smith |
| 2009/0258836 A1* | 10/2009 | Civan .................. A61P 27/02 514/46 |
| 2010/0241008 A1 | 9/2010 | Belleville et al. |
| 2010/0312125 A1* | 12/2010 | Zhang .............. A61B 5/02116 600/485 |
| 2011/0313300 A1* | 12/2011 | Quinn .............. A61B 5/02225 600/485 |
| 2013/0046190 A1* | 2/2013 | Davies ................ A61B 5/0215 600/486 |
| 2013/0172734 A1 | 7/2013 | Hsieh |
| 2013/0216481 A1* | 8/2013 | Rosenmeier ....... A61K 49/0004 424/9.1 |
| 2013/0246034 A1* | 9/2013 | Sharma ................ A61B 6/503 703/11 |
| 2014/0181717 A1* | 6/2014 | Lahti .................... A61B 5/742 715/771 |
| 2014/0276139 A1 | 9/2014 | Burkett et al. |
| 2014/0276140 A1* | 9/2014 | Kinghorn ............ A61B 5/0456 600/486 |
| 2015/0105673 A1* | 4/2015 | Gregorich ......... A61B 5/02007 600/480 |
| 2016/0000341 A1* | 1/2016 | Rotman .............. A61B 5/0215 600/486 |
| 2016/0058307 A1* | 3/2016 | Svanerudh .......... A61B 5/0066 600/427 |
| 2016/0120415 A1* | 5/2016 | Webler .............. A61B 5/02158 600/486 |
| 2016/0228071 A1* | 8/2016 | Wang .................... A61B 5/339 |

FOREIGN PATENT DOCUMENTS

| | | |
|---|---|---|
| EP | 3021741 | 10/2019 |
| WO | 2001013779 | 3/2001 |
| WO | 2004110279 | 12/2004 |
| WO | 2013028612 | 2/2013 |
| WO | 2014163334 | 10/2014 |

* cited by examiner

SYSTEM AND METHOD FOR EVALUATING BLOOD FLOW IN A VESSEL

BACKGROUND

The present disclosure generally relates to assessment of blood flow in vessel for determining a severity of a blockage or other restriction to the flow of fluid therethrough, and more particularly to methods and systems for automatically determining a reliable fractional flow reserve value.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides a measure of stenosis severity that allows determination as to whether the blockage limits blood flow within the vessel to an extent that treatment is required. The normal value of FFR in a healthy vessel is 1.00, while values less than a threshold FFR value are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for evaluating blood flow in a vessel of a patient includes a catheter containing a first pressure sensor and a second pressure sensor and configured to simultaneously measure pressure data within a vessel on a first side of a stenosis and a second side of a stenosis. The pressure data generated by the catheter includes a first series of pressure measurements from the first pressure sensor positioned on the first side of the stenosis and a second series of pressure measurements from the second pressure sensor positioned on the second side of the stenosis. The system further includes an FFR calculation module executable on one or more processors and configured to calculate a stability index for each of two or more portions of the pressure data, wherein each stability index indicates at least one of heart rate stability and catheter stability for the respective portion of the pressure data. An optimal time window is identified for calculated fractional flow reserve (FFR) based on the pressure data, wherein the optimal time window is determined based on the stability indexes. An FFR value is then calculated based on the pressure data in the optimal time window, and the FFR value is then outputted to the clinician.

In one embodiment, a method of evaluating blood flow in a vessel of a patient includes receiving pressure data measured in the vessel being evaluated. The pressure data includes a first series of pressure measurements from a first pressure sensor positioned on a first side a stenosis within the vessel, and a second series of pressure measurements from a second pressure sensor positioned on the second side of the stenosis within the vessel. A stability index is then calculated for each of two or more portions of the pressure data, wherein each stability index indicates at least one of heart rate stability and catheter stability for the respective portion of the pressure data. An optimal time window for calculation of FFR is then identified based on the stability indexes. An FFR value is then calculated based on the pressure data in the optimal time window.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
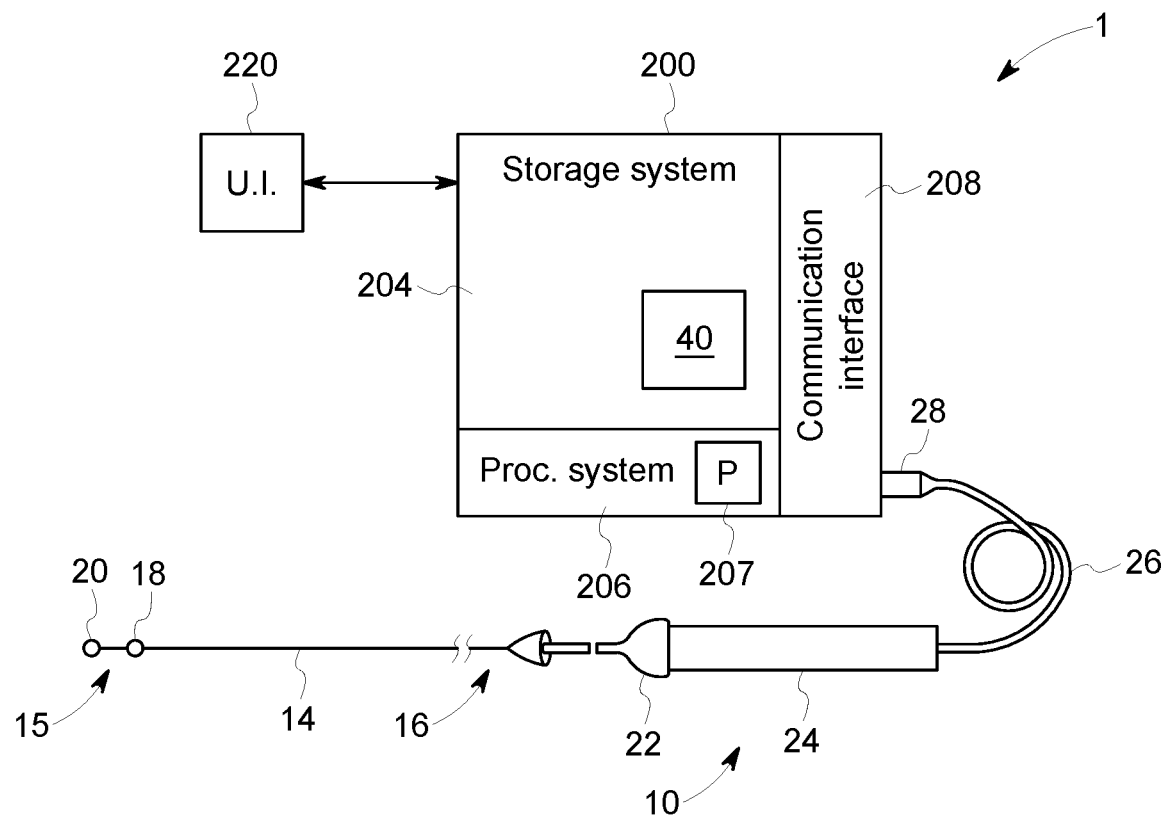
FIG. 1 depicts one embodiment of a system for evaluating blood flow in a vessel according to the present disclosure.

Current systems for measuring the proximal and distal pressures on either side of a stenosis in a vessel and calculating FFR generally rely on the administering clinician's input to define the monitoring period. Namely, most systems are configured such that a clinician pushes a button to start and stop a monitoring period. A running FFR value is determined based on the pressure data during the period between the start input and the end input, and the final FFR value output is taken as the lowest FFR calculated during that period instructed by the physician.

FFR is the ratio of maximum blood flow distal to a stenotic lesion to the normal maximum flow in the same vessel. Specifically, FFR is calculated using the following pressure ratio: $FFR = P_d/P_a$, where $P_d$ is the pressure distal to the lesion and $P_a$ is the pressure proximal to the lesion. Thus, an FFR of 1.0 means that the stenosis is not inhibiting any flow, as the pressure distal to the stenosis is the same as the pressure proximal to the stenosis. However, the FFR value is not calculated based on comparison of single pressure values because such a calculation would be overly influenced by noise or transient aspects of the measurement. Accordingly, the FFR value is typically calculated based on mean arterial pressures over a period of time, such as a single heart beat or a set number of heart beats. By utilizing pressure data over a period of time, the influence of noise and other artifacts is minimized. Likewise, by utilizing data over multiple heart beats, variation between heart beats can also be minimized. For example, an FFR value can be calculated over a period of time based on a running average of the ratio for a particular number of beats.

In current systems, an output FFR value is automatically selected by the system as the lowest running FFR value over the time period indicated by the physician. Generally, an FFR value lower than 0.75 indicates a hemodynamically significant stenosis. An FFR value higher than 0.8 indicates a stenosis that is not hemodynamically significant. Values between 0.75 and 0.8 are intermediate, and are generally considered in the context of a patient's clinical history to determine if revascularization is necessary.

In many current embodiments, the FFR value and the calculation window providing the basis for the FFR calculation are outputted such that the clinician can view the information. In many available systems, clinicians are provided the ability to adjust the time period selected for the FFR, and thus to select a different location in the pressure wave for calculation of the FFR. Through their experimentation and research, the inventors have recognized that physicians adjust the calculation window for FFR a majority of the time. Thus, the inventors have recognized that current automated methods for determining FFR are inaccurate, and usually require adjustment by the clinician.

Moreover, the inventors have conducted significant research and case studies relevant to FFR, the inventors have recognized that significant inconsistencies exist in when and how clinicians adjust the FFR calculation window. Accordingly, the inventors have recognized that significant inconsistencies exist in how FFR is calculated based on the measured pressure data, and thus inconsistencies in when stents are utilized. The inventors' studies have revealed that, especially in the "gray area" of values (e.g., between FFR values of 0.75 and 0.80), where clinicians are making judgment calls on whether to utilize a stent, inconsistencies in the selection of the data window for calculation of the FFR significantly influence the outcome of the revascularization determination. Namely, the studies indicated that decisions on whether to use revascularization in borderline cases are inconsistent and seemingly arbitrary. The inventors have found this to be the case even when comparing data on procedures performed by the same physician, as consistent numerical support and/or patterns cannot be discerned to predict when revascularization will be selected based on the FFR data. Accordingly, the inventors have recognized that an improved numerical approach for calculating and assessing FFR is necessary for creating more consistent and repeatable revascularization outcomes based on FFR.

In view of their recognition of the problems and challenges in the relevant art, the inventors have developed the disclosed improved methods for identifying optimal pressure values for FFR calculations so as to achieve consistent FFR calculations and numerically supportable revascularization outcomes. For example, the optimal time window may be identified based on a running average of the pressure data over a predetermined number of heart beats, or based on other calculations indicating one or both of heart rate stability and catheter stability. For example, the FFR calculation module may calculate a one or both of heart rate instability value (such as a percentage variation in heart rate) and catheter instability value (such as based on the frequencies present in the pressure data), and stability index may be based on one or both of those instability values. The optimal time window for FFR calculation is then identified based on the stability index, and the FFR value is calculated and outputted accordingly. Thereby, a mathematical framework is provided for identifying an optimal time window for calculation of an FFR value. Accordingly, variation in FFR calculation can be eliminated and better discrimination can be provided for the FFR calculation so that revascularization decisions can be made on consistent and reliable information.

Figure 2:
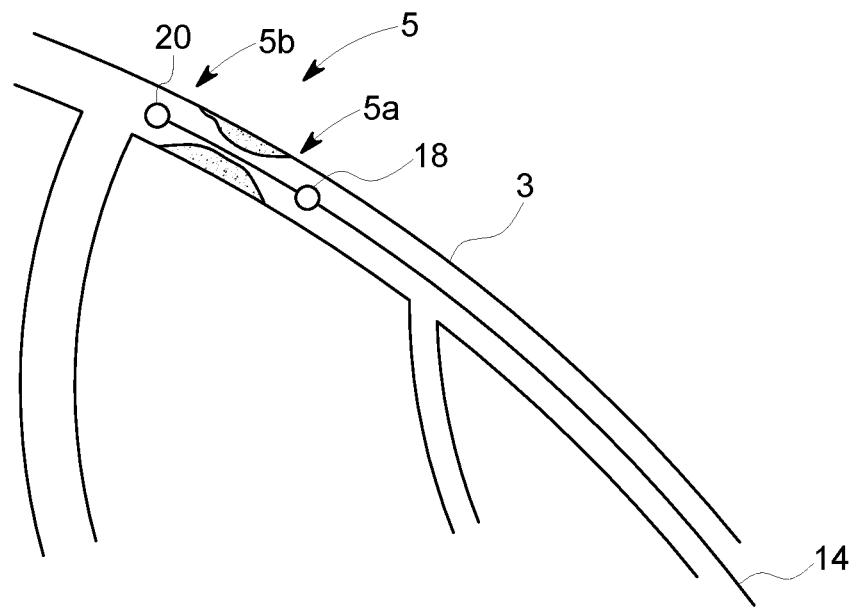
FIG. 2 depicts an exemplary pressure sensing catheter measuring pressure data within a vessel.

FIG. 1 depicts an exemplary system 1 for evaluating blood flow based on pressure measurements. Specifically, the system includes a catheter 10 containing a first pressure sensor 18 and a second pressure sensor 20. With reference also to FIG. 2, the first pressure sensor 18 is configured to be positioned on a proximal side of the stenosis 5 to the catheter system in order to measure a first series of pressure measurements. The second pressure sensor 20 is positioned on the distal side of the stenosis 5 and is configured to a second series of pressure measurements, which are time synchronized with the first series of pressure measurements, from the distal side of the stenosis 5. The pressure sensors are generally on a distal end 15 of a wire 14 that is passed through the vessel 3 from an entrance point to the stenosis area 5. Various catheters may provide different distances between the first pressure sensor 18 and the second pressure sensor 20. For example, most catheters 10 provide a distal end 15 of the pressure sensing wire 14 having pressure sensors 18, 20 that are spaced out within a range of 0.75 inches to 2 inches. The second pressure sensor 20 may be provided at the distal tip of the wire, or slightly proximal to the distal tip, such as 20 mm away from the distal tip. The pressure sensors 18, 20 may be any of various types of pressure sensors incorporated into catheters 10 for vascular pressure measurement application. For example, the pressure sensors 18, 20 may be piezo-resistive pressure sensors, piezo-electric pressure sensors, capacitive pressure sensors, electromagnetic pressure sensors, optical pressure sensors, fluid column pressure sensors, and/or combinations thereof.

The pressure sensing wire 14 has a proximal end portion 16 that connects to a catheter base 24, which is the hand held portion of the catheter maneuvered and operated by the clinician during the procedure. The wire portion of the catheter 10 may be disposable, or otherwise removable for sterilization, and may connect to the catheter base 24 at a connector 22 configured to connect to the proximal end portion 16 of the pressure sensing wire 14. A cable 26 connects to an opposing end of the catheter base 24 and is flexible such that the catheter 10 is maneuverable as necessary during the procedure. The cable 26 terminates at a module connecter 28 configured to connect to a computing system 200.

The computing system 200 includes a communication interface 208 configured to receive and transmit information between the catheter 10 and the processing system 206. For example, the communication interface 208 may be configured to receive pressure measurements from the first and second pressure sensors 18, 20. In various system configurations, the pressure measurements may be received at the communication interface 208 in either analog or digital form. In certain embodiments, signal processing hardware and digitization may be housed in the catheter base 24 to filter, amplify, and/or digitize the pressure measurement signals. In other embodiments, the raw analog pressure measurement information may be received and digitized at the communication interface 208 of the computing system 200. The computing system 200 further includes a processing system 206 comprised of one or more processors 207 and storage system 204 storing software, including the FFR calculation module 40, as well as other needed data and information. The FFR calculation module is configured to identify an optimal time window within the pressure data from the pressure sensors 18, 20 for calculating an FFR value based on the methods disclosed herein. The optimal window is a time segment with stable electrical activity of the heart muscle and stable conduction. Those conditions are measured by a median or mean value of QRS duration and RR interval. To further improve the consistency of the measurement, a series of overlapped time windows may be used and the median or mean value of the series measurements utilized. Information regarding the FFR value and the optimal time window may then be displayed on the user interface 220 for review and verification by a clinician. Alternatively or additionally, the FFR value and the optimal time window may be stored in the storage system 204 and/or in the patient's relevant medical record.

Figure 3:
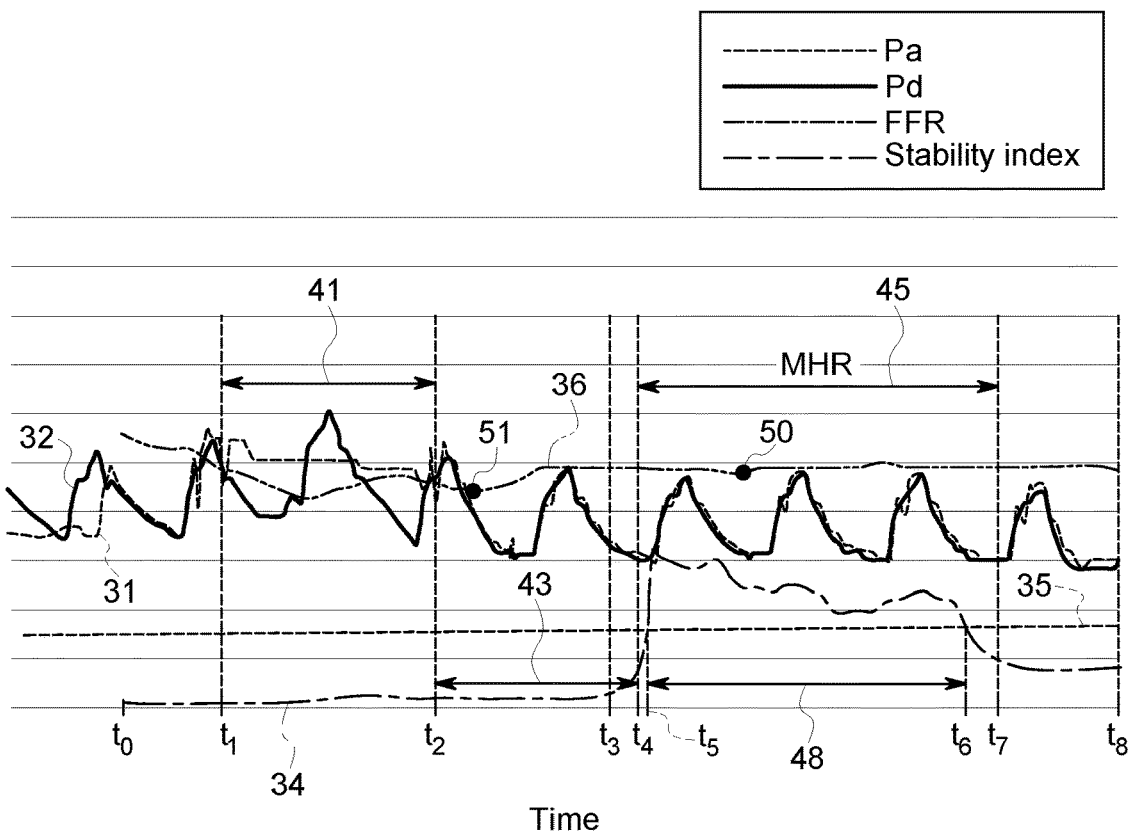
FIG. 3 is a graph depicting exemplary pressure data and a stability index and FFR according to the present disclosure.
Figure 4:
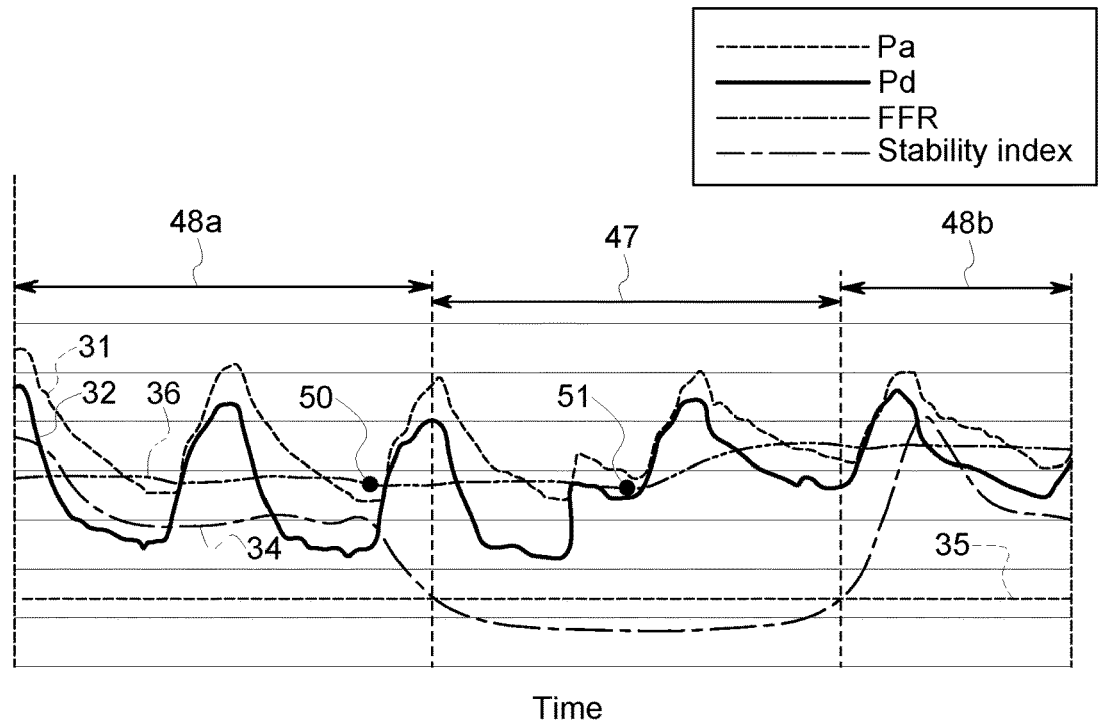
FIG. 4 is another graph depicting pressure data and stability index and FFR calculations depicting another example according to the present disclosure.

FIGS. 3 and 4 are graphs depicting exemplary pressure data, including a first series of pressure measurements 31 based on output of a first pressure sensor and a second series of pressure measurements based on output of a second pressure sensor. FIG. 3 depicts the pressure data 31 and 32 prior to, during, and after injection of a hyperemic agent. As will be known to a person having ordinary skill in the art, hyperemic agents, such as adenosine, can be administered by injecting a bolus into the patient via intravenous catheter or by drip administration via the intravenous catheter. The half-life of most hyperemic agents is short. For example, the half-life of adenosine is less than 10 seconds. Thus, the window of opportunity for recording FFR is narrow. There is an initial settling period where the hyperemic agent takes effect and the heart rate reaches an elevated and steady level. Following the settling period, the maximal hyperemic region (MHR) offers the region for best and most accurate detection of FFR. Determining the MHR, the time period of maximum hyperemia, relative to administration of various types of hyperemic agent is an important part of accurately determining FFR because including data during periods other than the MHR can lead to an inaccurate FFR determination.

FIG. 3 depicts pressure data, including a first series of pressure measurements 31 and a second series of pressure measurements 32 over a period of time during which a bolus of hyperemic stimulus agent is administered to a patient and the maximum effect period of the hyperemic stimulus agent. The FFR is represented at line 36 on the graph. The bolus of hyperemic agent is administered in the injection period 41 between $t_1$ and $t_2$, and the drug takes effect during the settling period 43 between $t_2$ and $t_3$. As illustrated, the FFR 36 is unsteady prior to and after the MHR 45, decreasing during the injection period 41 and during the settling period 43, where the heart rate and pressure measurements fluctuate due to administration of the hyperemic agent. Thus, inclusion of data during this period, such as including data during the settling period 43 would yield an artificially low FFR value. Likewise, the FFR 36 decreases after the MHR 45, when the agent is wearing off and thus the heart rate becomes unsteady.

In other embodiments where the hyperemic agent is administered via an intravenous drip, the "injection period" where the drug is administered is much longer and overlaps with the measurement period. In most existing systems where drip hyperemic drug administration protocols are used, the FFR calculation window is enable for a long period of time (e.g., 2 minutes) during administration of the hyperemic drug drip. The chance of artifact introduction during that long recording period is extremely high, which is likely to cause an erroneously low FFR output.

The inventors have recognized that systems and methods are needed for identifying an optimal pressure data for calculation of FFR, and that such an optimal window is one in which the pressure data measurements are relatively stable and are not influenced by variables such as an unstable heart rate or influenced by noise, such as caused by false pressure measurement resulting from instability or movement of the measurement catheter 10. Ideal FFR values are calculated from pressure data in regions of high stability that are not influenced by heart rate variability and/or noise, such as due to false pressure measurement resulting from movement of the catheter. The MHR represents the time section of pressure data where the heart rate is fully influenced by the hyperemic agent and is at a maximum stability. Thus, the most reliable FFR value will be available in that region of the data.

Prior art systems do not identify the most stable region in the pressure data for detection of FFR instead typically utilize the entire section of data following the physician's recording trigger. This will usually include data during the settling period 43, which as shown in the depicted example, will often yield erroneously low FFR values. Referring again to the example at FIG. 3, if data during the settling period 43 were to be included in the time window for calculation of the FFR, the minimum FFR represented at point 51 would be selected as the FFR value automatically outputted by the system. However, the FFR value calculated during the settling period 43 is erroneously low. Instead, in a system according to the present disclosure identifying and only utilizing data during the MHR 45, then a more accurate and reliable FFR value 50 is identified.

The optimal time window 48 for calculation of the FFR value is determined based on a stability index 34. The inventors have recognized that various methods may be utilized for calculating the stability index and identifying the optimal window 48. In the depicted embodiment, the stability index 34 is calculated as a weighted running two second standard deviation of mean pressures calculated based on the first pressure data 31 and the second pressure data 32. For instance, where the sample rate for the pressure meausurement is 240 hz, the FFR value is calculated at each sample using an average of the number of samples equal acquired over the last three heartbeats (roughly 184 samples). This produces an FFR value for each sample. In one instance illustrating this example, the hypothetical stability function at each sample looks back over the last second (240 samples) and forward one second (240 samples) and feeds those 480 samples into the excel equation=1/STDEVA(F1:F480)*90. So the stability index at each sample is inversely proportional to the standard deviation of the FFR values for the two second window around that sample, with 90 being an arbitrary scaling factor to make the stability index graph decently with the Y-axis of the FFR and pressure plot. Note that additionally, the region chosen for that graph is around the case time of the drug injection, illustrating incorporation of the drug injection intelligence to the stability equation to limit the equation active window.

In the depicted example, where the stability index 34 is calculated as a weighted running two second standard deviation calculation, the first stability index value is available at time $t_0$. Namely, the first stability index value is calculated based on the pervious two-second portion of the pressure data 31, 32, and then is continually calculated as a running average over the previous two second portion. The running FFR value 36 is also calculated based on a previous time section of pressure data 31, 32. In the depicted embodiment, the running FFR calculation 36 also starts at time $t_0$. In other embodiments, the first value of the running FFR calculation 36 may be at a different time from the first value of the running stability index 34. However, in certain embodiments, it may be beneficial to calculate the stability index based on an amount of pressure data that is relevant to the amount of time used for calculating the running FFR. Thereby, the running stability index 34 will provide a stability value most relevant to and translatable to the FFR calculation, as both calculations will be performed on the same or similar time period of pressure data.

In certain examples, an optimal time window 48 for calculation of FFR may be identified as the period of time for which the stability index 34 exceeds a threshold index value 35. The threshold index value 35 may be a preset value, which may account for certain variables, such as the type of catheter 10 being employed, the type of procedure being performed, the location and characteristics of the vessel being explored, and/or physician input. In certain examples, the threshold index value 35 may be selectable by the clinician performing the procedure. In other embodiments, the threshold index value 35 may be calculated based on the pressure data 31, 32 being measured during the procedure, as well as the ongoing stability index 34 calculated based thereon. The determination of the threshold index value 35 may also account for certain variables of the procedure, such as the patient's physiological condition and/or the time constraints of the procedure. For example, the threshold index value 35 may be set lower for patients with arrhythmias or other heart conditions generating an unstable heart beat. Alternatively or additionally, therefore a longer data series might be needed to compensate variations for the final FFR value or atrial fibrillation patients because a relatively stable RR interval may be more difficult to find. To measure the electrical stability of the heart condition, a series arrhythmia detections is conducted to rule out any supraventricular/ventricular premature heart beats from the optimal time window 48. The threshold index value 35 may also be calculated to account for the time constraints of a particular procedure. For example, the threshold index value may be lowered where the stability indicator remains low throughout the maximal hyperemic region (MHR), and thus an optimal time window 48 providing sufficient data for calculation of the FFR will not be identified unless the threshold index value 35 is lowered. In such an embodiment, an alert may be generated to the clinician notifying the clinician that the threshold index value 35 was lowered in order to obtain the requisite and sufficient data for calculation of the FFR. Alternatively, in certain examples, the running stability index values may be presented in conjunction with the running pressure and FFR values to aid a clinician in manually selecting a valid FFR point.

In certain embodiments, a heart rate instability indicator may be calculated for detection of the MHR 45. For example, the heart rate instability indicator may be percentage variation in heart rate for each heart beat interval of pressure data. Thus, the heart rate instability indicator will be calculated for each heart beat interval of pressure data by comparing a duration of each heart beat interval to one or more previous heart beat intervals. In certain examples, the MHR may be identified where the heart rate instability indicator reaches a sufficiently low threshold to indicate relatively low instability, or variation, in heart rate. The threshold heart rate instability threshold may be a preset value, or may be determined based on previous heart rate data or health information for the patient, such as information relevant to an existing heart condition for the patient that could influence the consistency of the patient's heart rate.

Alternatively or additionally, the optimal time window 48 may be determined to exclude heart beats initiated by a pace maker. Many hemodynamic patients have internal pace makers that are not shut off during hemodynamic procedures. At times these detect abnormal heart beat and become active and start pacing the heart, thereby creating artificial stability in the heart rate due to an external force that may not result in a good FFR value. Accordingly, the system 1 may also detect this and use it as a basis for identifying heart rate instability.

In certain embodiments, the method for identifying the optimal time window 48 may also include estimation of a period when the hyperemic agent is most likely to have maximal effect on the patient based on drug administration values and patient information. For example, the system 1 may be configured to estimate an earliest likely time for the MHR based on at least one of a time of administration of a hyperemic stimulus agent (e.g., $t_0$-$t_1$), a type of hyperemic stimulus agent administered, the dose of hyperemic stimulus agent administered to the patient, and a body mass index (BMI) of the patient. Likewise, an estimated end time may also be determined by the system based on the foregoing values relevant to the drug administration. The estimated time window between the estimated start time and the estimated end time can then be utilized to narrow the possible time in which the optimal time window 48 can be identified. For example, the system 1 may be configured to start comparing the running stability index 34 to the threshold index value 35 after the estimated start time. Thereby, values occurring during some or most of the settling period 43 can be eliminated. In the depicted example, the estimated start time based on the values relevant to drug administration is at time $t_3$, which eliminates much of the settling period 43, including the errant low FFR value 51. Thus, in certain embodiments where the running stability index 34 surpasses the threshold index value 35 during the settling period, such data can still be ruled out based on the estimated time window. Similarly, data falling after the estimated end time, which in the depicted example is $t_8$, could also be eliminated from the possible time period considered for the optimal time window 48.

In certain embodiments, the possible period of the optimal time window 48 may further be narrowed based on detection of the MHR. As described above, the MHR is determined based on the heart rate, such as the heart rate exhibited in the pressure data 31, 32, and is the period for which the heart rate is stable and maximally effected by the hyperemic stimulus agent. Thus, identification of the MHR can be helpful in identifying the optimal time window 48. In certain embodiments, the MHR 45 may be identified based on the heart rate exhibited in the pressure data 31, 32, and identification of the optimal time window 48 may be confined to the MHR 45. For example, the system 1 may be configured to start analyzing the running stability indicator 34 for detection of the optimal time window 48 once the start of the MHR 45 has been identified. Similarly, the optimal time window 48 identification process may cease upon termination of the MHR 45.

Alternatively or additionally, the system 1 may be configured to identify the MHR based on the heart rate instability indicator in combination with the estimated window analysis described above. For example, the system may begin calculation and/or analysis of the heart rate instability indicator at the estimated start time $t_3$ for the estimated maximal effect window. Similarly, the termination of the MHR 45 is calculated based on the heart rate. For example, the MHR 45 may be terminated once the heart rate instability indicator increases passed the threshold heart rate instability value. The termination of the MHR 45 may similarly be determined based on the estimated time window, such that the MHR 45 is not permitted to extend beyond the estimated end time $t_8$.

In the depicted embodiment, the MHR 45 extends between time $t_4$ and time $t_7$. The optimal time window 48 is identified as the period within the MHR 45 during which the running stability index 34 is greater than the threshold index value 35. In the depicted example, the optimal time window 48 is identified as the period between time $t_5$ and time $t_6$. The FFR value 50 that gets outputted by the system 1 is calculated based on the pressure data 31 and 32 within that optimal time window 48. For example, in the depicted embodiment the running FFR value 36 is calculated as a running average of three heart beat intervals in the pressure data. The final outputted FFR value is then determined to be the lowest running FFR value 36 within the optimal time window 48, which is represented at point 50.

In certain embodiments, the optimal time window 48 may further be narrowed to eliminate periods of noise due to catheter instability or the presence of other noise-creating factors. If the catheter 10 is moved within the vessel 3, pressure changes will be sensed by the pressure sensors 18 and 20 that do not reflect actual changes of pressure within the vessel 3. Such movement of the catheter wire 14 within the vessel 3 can cause high frequency noise within the pressure data 31, 32, as well as baseline drift. The stability index 34 can be utilized to eliminate noisy periods due to catheter instability from the pressure data used for calculation of FFR. For example, if the running stability index 34 falls below the index threshold 35, the optimal time window 48 may be amended to exclude the pressure data 31, 32 for the period where the running stability index 34 is below the index threshold 35. FIG. 4 exemplifies such a situation, where catheter instability causes baseline drift and high frequency noise, both of which impact the calculated FFR value. The region of instability 47 where the running stability index 34 falls below the threshold index value 35, is removed from the optimal time window 48. Accordingly, the optimal time window is bifurcated into a first optimal time window portion 48a and a second optimal time window portion 48b. The running FFR calculations 36 thus available for determination of the final outputted FFR value are thus those running FFR calculations during the first and second optimal time periods 48a, 48b. The running FFR calculations 36 during the instability period 47 are thus excluded from the possible FFR values from which the final FFR value can be determined. Accordingly, the actual low point of the running FFR curve, which is point 51, is eliminated from the possible values from which the final outputted FFR can be chosen because it falls during the instability region 47 where the data is inaccurate, and thus FFR value 51 is erroneously low. Instead, the outputted FFR value 50 is selected, which falls during the first optimal time period 48a, and constitutes the lowest running FFR value calculated during the optimal time window period 48a and 48b.

In various embodiments, the stability index may be calculated based on other methods than the running standard deviation method described above. To provide just one example, the stability index may be a value scale, where one end of the value scale represents stable pressure data that will result in a reliable FFR calculation, and the other end of the scale represents highly unstable data that will result in an errant FFR calculation. The scale may be represented as any range of values, such as between 0 and 1, between 1 and 10, etc. In other embodiments, the stability index may be just one of two values, where one value represents stable data that can be utilized in the FFR calculation and the other value represents unstable data that cannot be used in the FFR calculation. In such an embodiment, the stability index could be a 1 or 0, where 1 indicates stable data and 0 indicates unstable data. In such an embodiment, the stability index may be set to a value of 1, indicating stable data, where the heart rate instability indicator is below a threshold heart rate instability and the catheter instability is below a threshold catheter instability value, thus indicating a stable heart rate and a lack of high frequency noise or baseline drift caused by catheter instability.

For example, the stability index may be calculated based on the heart rate instability indicator described above and/or based on other values calculated to indicate stability aspects of the pressure signal. In certain examples, a separate catheter instability value may be calculated, such as based on the presence of high frequency within the pressure data 31, 32 and/or the presence of baseline drift. The stability indicator may be calculated based on both the catheter instability indicator and the heart rate instability indicator. In that example, the stability indicator may be set to 0 when either the heart rate instability indicator exceeds the threshold heart rate instability or the catheter instability indicator exceeds a threshold catheter instability. Such an embodiment would enable determination of an optimal time window 48 that avoids regions of unstable heart rate and noise due to catheter instability.

In still other examples, factors accounted for in the stability index and determination may include: 1) high and low heart rate thresholds to eliminate excessively high heart rate zones (regardless of stability) and/or eliminate excessively low heart rate zones (regardless of stability); 2) high and low blood pressure thresholds to eliminate periods where non-invasive or invasive blood pressures are above or below respective thresholds; 3) pace maker activity indicators to eliminate periods where an internal pace maker is active; 4) x-ray activity to gate the zone of interest to only when x-ray is active; 5) respiration activity measurements (because blood pressure is most stable between breaths); 6) ultrasound doppler blood flow measurements.

Figure 5:
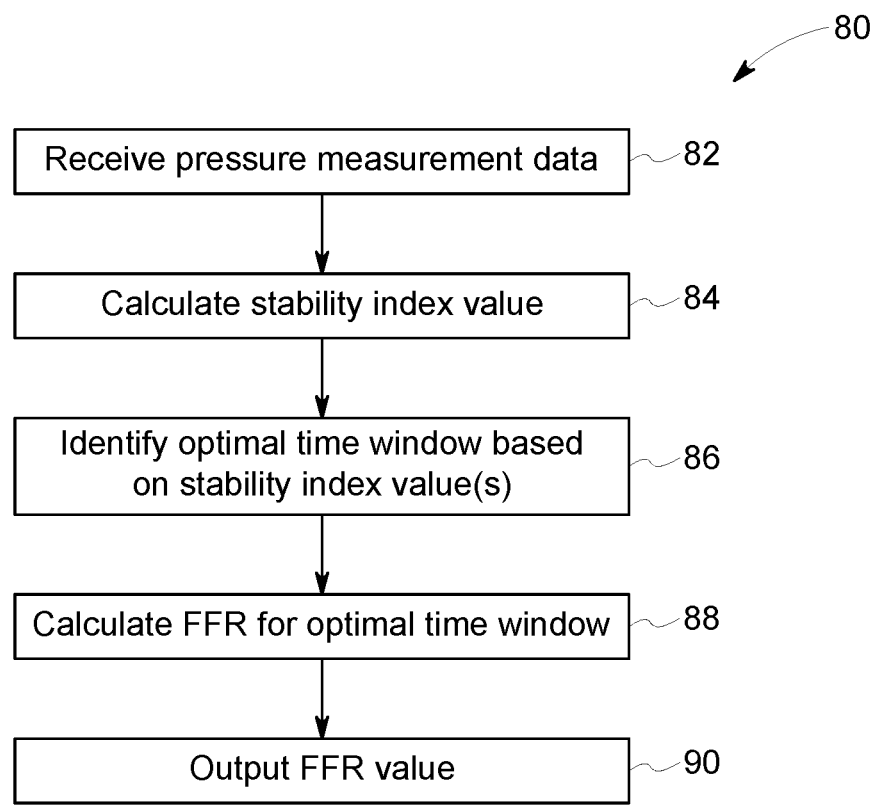
FIGS. 5-7 depict exemplary methods, or portions thereof, for evaluating blood flow in a vessel of a patient according to the present disclosure.
Figure 6:
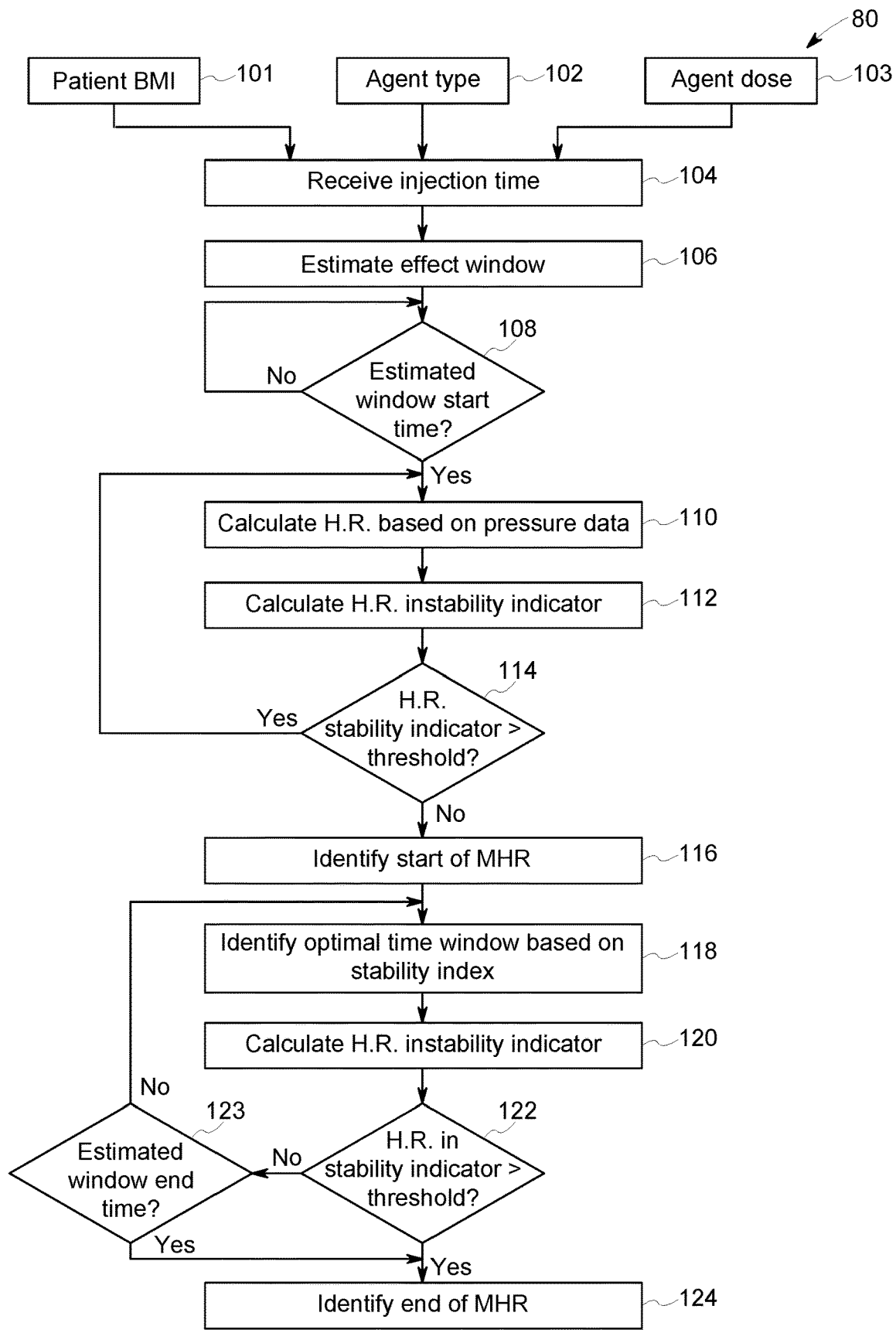
Figure 7:
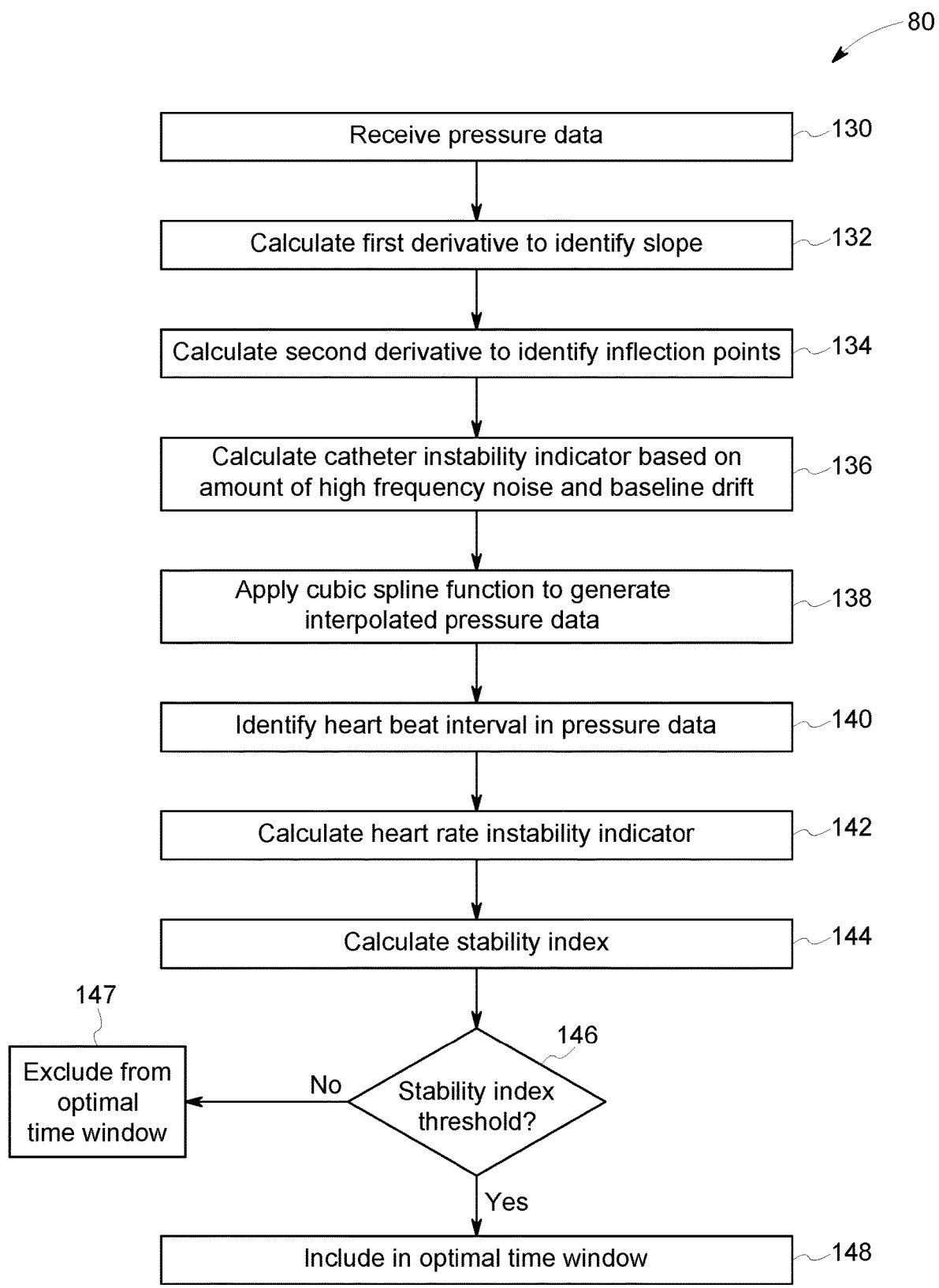

FIGS. 5-7 depict exemplary methods 80, or portions thereof, of evaluating blood flow in a vessel for determining the impact of a stenosis. In the example at FIG. 5, pressure measurement data is received at step 82, which includes pressure measurements from first and second pressure sensors. A stability index value is calculated at step 84 based on the pressure measurement data—e.g., based on a section of the first and second series of pressure measurements. The stability index value may be any value capable of conveying the stability of the pressure measurement data received at step 82 as compared to previously-received pressure measurement values. For example, the stability index may account for the stability of the heart rate reflected in the pressure measurement data, as well as the stability of the catheter making the measurements. Numerous exemplary stability index values are described in the present disclosure. However, a person of ordinary skill in the art will recognize in view of the information provided in the present disclosure, that the stability index may be calculated and indicated in any number of ways. An optimal time window is identified at step 86 based on the stability index values. For example, the stability index value calculated at step 84 may be compared to a threshold index value to determine whether the optimal time window can extend to include the portion of pressure measurement data captured by the stability index value.

The FFR value is calculated at step 88. In certain embodiments, the FFR value may be a running FFR calculation, as is exemplified in FIG. 3. In other embodiments, the FFR calculation may be performed upon identification of the optimal time window based on the pressure measurement data within that time window. An output FFR value is then identified at step 90 and is provided as an output of the FFR calculation module 40. For example, the selected FFR value for output may be displayed on the user interface 220 associated with the computing system 200. In certain embodiments, the selected FFR value may be displayed along with a graph similar to that in FIG. 3 depicting the pressure data 31, 32 and corresponding running FFR calculation 36. In certain embodiments, the graph displayed on the user interface 220 may further include a line representing the running stability index calculation, where the series of values is exemplified as line 34 in FIG. 3.

FIG. 6 depicts another embodiment of a method 80 of evaluating blood flow in a vessel according to the present disclosure. A patient's BMI is received at step 101, an agent type is received at step 102, and an agent dose is received at step 103. The system may further receive indication of an administration method, such as bolus or drip. An injection time is received at step 104, which could be, for example, a start time of a bolus injection or of a drip administration of a hyperemic stimulus agent. An estimated effect window is then determined at step 106, which includes an estimated earliest start time and an estimated latest end time for the maximal effect of the hyperemic stimulus agent. Step 108 is executed to wait for the estimated window start time. Once that estimated window start time is reached, then a heart rate is calculated at step 110 based on the pressure data. A heart rate instability indicator is calculated at step 112. For example, the heart rate instability indicator may be calculated as a percentage variation of the duration of each heart beat interval compared to durations of one or more previous heart beat intervals within the pressure data. The heart rate instability indicator is compared to a threshold heart rate instability value at step 114. The heart rate reflected in the pressure data continues to be monitored until the heart rate instability indicator is below the threshold heart rate instability at step 114, at which point the start of the MHR is identified at step 116. The system then looks for identification of the optimal time window at step 118. For example, the optimal time window may be identified as the period during which the stability index exceeds a threshold index value. The system continues to calculate the heart rate instability indictor at step 120 and compare the heart rate instability indicator to the threshold instability value at step 122. So long as the heart rate and stability indicator remains below the threshold instability value, then the system continues to look for the optimal time window based on the stability index. Once the heart rate instability indicator reaches or exceeds the threshold, then the end of the MHR is determined at step 124. This also terminates the assessment and identification of the optimal time window.

FIG. 7 depicts another embodiment of a method 80, or portion thereof, for evaluating blood flow in a vessel of a patient. The pressure data is received at step 130, and then steps are executed to determine a catheter instability indictor based on the pressure data. In certain embodiments, the data may be interpolated to eliminate high frequency noise from the pressure waveforms and to minimize baseline drift, which are common pitfalls for creating errant FFR analysis. In this specific example, a first derivative is calculated at step 132 for each of the first and second series of pressure measurements to identify a slope of the respective pressure measurement waveform. A second derivative is calculated at step 134 for each of the respective series of pressure measurements to identify inflection points within the respective pressure waveforms. A catheter instability indicator is then calculated at step 136 based on an amount of high frequency noise and baseline drift present in a respective window of the pressure data. For example, the high frequency noise may be determined based on the first and second derivative information calculated at step 132 and 134. Various methods for determining the baseline drift are well known in the art. The cubic spline function is applied at step 138 to interpolate the pressure data in order to reduce the presence of high frequency noise and baseline drift exhibited in the respective waveforms. A heart beat interval is then determined at step 140 based on the pressure data and a heart rate instability indicator is determined at step 142.

The stability index is then calculated at step 144. For example, the stability index may be calculated based on the heart rate instability indicator calculated at step 142 and the catheter instability indicator calculated at step 136. The stability index is then compared to a threshold index value at step 146, and the optimal time window is determined based on the comparison. In the depicted example, high stability index values indicate signal stability and low stability index values indicator signal instability. Thus, step 146 assess whether the stability index exceeds the relevant threshold index value. In other embodiments, the stability index value may be reversed, where signal instability is signified by high stability index values and signal stability is indicated by low stability index values. In such an embodiment, logic would be executed at step 146 to determine whether the stability index is less than the respective threshold index value. Where a stability index value indicating signal stability is identified, the corresponding data is made available for the FFR calculation by including the time period within the optimal time window at step 148. Conversely, if the stability index indicates instability of the relevant pressure signals, then the corresponding pressure data is excluded from the FFR calculation at step 147. The FFR value is then calculated based on the optimal time window as is described above.

Referring again to FIG. 1, the various methods 80 of evaluating blood flow in a vessel may be executed and controlled by the computing system 200 receiving pressure data from the catheter 10. The computing system 200 includes a processing system 206, storage system 204, and a communication interface 208. The processing system 206 loads and executes software 202 from the storage system 204, including the FFR calculation module 40, which is an application within software stored in the storage system 204. The FFR calculation module 40 includes computer-readable instructions that, when executed by the computing system 200 (including the processing system 206), direct the processing system 206 to operate as described in herein in further detail, including to determine the optimal time window for the FFR calculation.

Although the computing system 200 as depicted in FIG. 1 includes one FFR calculation module 40, it should be understood that one or more software elements having one or more modules may provide the same operation, which may be distributed across multiple storage locations. Similarly, while description as provided herein refers to a computing system 200 and a processing system 206, it is to be recognized that implementations of such systems can be performed using one or more processors, which may be communicatively connected, and such implementations are considered to be within the scope of the description. For instance, portions of the storage system 204 storing certain instructions comprising the FFR calculation module 40, as well as portions of the processing system 206, may be housed within the catheter base portion 24.

The processing system 206 includes at least one processor 207, which may be a microprocessor, a general purpose central processing unit, an application-specific processor, a microcontroller, or any other type of logic-based device. The processing system 206 may also include circuitry that retrieves and executes software from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the FFR calculation module 40 may be stored on a separate storage device than pressure data and calculated FFR and stability index values. Storage system 204 may further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as to receive the first and second series of pressure measurements from the catheter 10. In certain embodiments, the communication interface 208 may include certain signal processing and digitization hardware and software for digitizing and processing the pressure signals from the pressure sensors 18, 20.

The user interface 220 is configured to receive input from a clinician, and display outputted FFR value(s) and other relevant information, as is described and exemplified herein. User interface 220 includes a digital display device and one or more input devices, which may include a mouse, a keyboard, a voice input device, a touch input device for receiving a gesture from a user, a motion input device for detecting non-touch gestures and other motions by a user, and other comparable input devices and associated processing elements capable of receiving input from a clinician. Speakers, printers, haptic devices and other types of output devices may also be included in the user interface 220.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for evaluating blood flow in a vessel of a patient, the system comprising:
    a catheter containing a first pressure sensor and a second pressure sensor and configured to simultaneously measure pressure data within a vessel on a first side of a stenosis via the first pressure sensor and a second side of the stenosis via the second pressure sensor;
    wherein the pressure data includes a first series of pressure measurements from the first pressure sensor positioned on the first side of the stenosis and a second series of pressure measurements from the second pressure sensor positioned on the second side of the stenosis;
    an FFR calculation module executable on one or more processors and configured to:
        calculate a stability index for each of two or more portions of the pressure data, wherein the stability index for each of two or more portions of the pressure data indicates at least one of heart rate stability and catheter stability for the respective portion of the pressure data;
        identify an optimal time window for calculating fractional flow reserve (FFR) based on the pressure data, wherein the optimal time window is determined based on the stability index for each of two or more portions of the pressure data;
        calculate an FFR value based on the pressure data in the optimal time window;
        administer a treatment to the patient when the FFR value is less than a threshold FFR value;
        wherein the FFR calculation module is further configured to calculate a catheter instability indicator based on an amount of high frequency noise and baseline drift present in the pressure data and wherein the stability index for each of two or more portions of the pressure data is based on the catheter instability indicator.

2. The system of claim 1, wherein the FFR calculation module is further configured to:
    compare the stability index to a threshold index value; and
    identify the optimal time window based on the comparison.

3. The system of claim 1, wherein the FFR calculation module is further configured to:
    calculate a heart rate instability indicator for each heart beat interval in the pressure data, wherein the heart rate instability indicator is a percentage variation of a duration of each heart beat interval compared to durations of one or more previous heart beat intervals.

4. The system of claim 3, wherein the FFR calculation module is further configured to identify the MHR based further on at least one of a time of administration of a hyperemic stimulus agent, a type of hyperemic stimulus agent administered, a dose of hyperemic stimulus agent administered, and a body mass index (BMI) of the patient.

5. The system of claim 3, wherein the FFR calculation module is further configured to:
  identify local maximums, local minimums, and/or inflection points in each of the first series of pressure measurements and the second series of pressure measurements;
  calculate the catheter instability indicator based on a frequency of the local maximums, local minimums, and/or inflection points; and
  wherein the stability index is based on at least one of the catheter instability indicator and the heart rate instability indicator.

6. The system of claim 1, wherein the FFR calculation module is further configured to:
  interpolate each of the first series of pressure measurements and the second series of pressure measurements to generate interpolated pressure data prior to calculating the FFR value, and calculate the FFR value based on the interpolated pressure data.

7. The system of claim 6, wherein the FFR calculation module is further configured to calculate a running average of a predetermined number of heart beat intervals of the interpolated pressure data throughout the optimal time window; and
  calculate the FFR value as a lowest running average value within the optimal time window.

8. The system of claim 1, wherein the stability index is calculated as a weighted running standard deviation of mean pressures calculated based on two or more portions of the pressure data.

9. A method of evaluating blood flow in a vessel of a patient, the method comprising:
  receiving pressure data measured in the vessel, the pressure data including:
    a first series of pressure measurements from a first pressure sensor positioned on a first side of a stenosis within a vessel;
    a second series of pressure measurements from a second pressure sensor positioned on a second side of the stenosis within the vessel;
  processing the pressure data by:
    calculating a stability index for each of two or more portions of the pressure data, wherein the stability index for each of two or more portions of the pressure data indicates heart rate stability and catheter stability for the respective portion of the pressure data;
    identifying, based on the stability index for each of two or more portions of the pressure data, an optimal time window within the pressure data for calculating fractional flow reserve (FFR);
    calculating an FFR value based on the pressure data in the optimal time window; and
    administering a treatment to the patient when the FFR value is less than a threshold FFR value
    wherein the method further comprises calculating a catheter instability indicator based on an amount of high frequency noise and baseline drift present in the pressure data and wherein the stability index for each of two or more portions of the pressure data is based on the catheter instability indicator.

10. The method of claim 9, further comprising comparing the stability index to a threshold index value; and
  identifying the optimal time window based on the comparison.

11. The method of claim 10, wherein a region of instability where the stability index falls below the threshold index value, is removed from the optimal time window.

12. The method of claim 9, wherein the stability index is calculated based on a running average of the pressure data over a predetermined number of heart beat intervals.

13. The method of claim 9, further comprising calculating a heart rate instability indicator for each heart beat interval in the pressure data, wherein the heart rate instability indicator is a percentage variation of a duration of each heart beat interval compared to durations of one or more previous heart beat intervals.

14. The method of claim 13, further comprising identifying a maximal hyperemic region (MHR) based on the heart rate instability indicator; and
  identifying the optimal time window to be within the MHR.

15. The method of claim 14, wherein the MHR is identified based further on at least one of a time of administration of a hyperemic stimulus agent, a type of hyperemic stimulus agent administered, a dose of hyperemic stimulus agent administered, and a body mass index (BMI) of the patient.

16. The method of claim 14, further comprising identifying local maximums, local minimums, and/or inflection points of each of the first series of pressure measurements and the second series of pressure measurements in the MHR;
  calculating the catheter instability indicator based on a frequency of the local maximums, local minimums, and/or inflection points; and
  wherein the stability index is based on at least one of the catheter instability indicator and the heart rate instability indicator.

17. The method of claim 9, further comprising identifying local maximums, local minimums, and/or inflection points of each of the first series of pressure measurements and the second series of pressure measurements;
  calculating the catheter instability indicator based on a frequency of the local maximums, local minimums, and/or inflection points; and
  wherein the stability index is based on the catheter instability indicator.

18. The method of claim 9, further comprising interpolating each of the first series of pressure measurements and the second series of pressure measurements to generate interpolated pressure data prior to calculating the FFR value, wherein the FFR value is calculated based on the interpolated pressure data.

19. The method of claim 18, wherein the interpolation includes applying a cubic spline function to each of the first series of pressure measurements and the second series of pressure measurements.

20. The method of claim 18, wherein the FFR value is calculated by determining a running average of a predetermined number of heart beat intervals of the interpolated pressure data throughout the optimal time window; and
  identifying a lowest running average value within the optimal time window.

21. The method of claim 9, wherein the high frequency noise is determined based on a first and a second derivative information and wherein the first derivative is calculated for each of the first and second series of pressure measurements to identify a slope of the respective pressure measurement waveforms and the second derivative is calculated for each of the respective series of pressure measurements to identify inflection points within the respective pressure waveforms.

22. A non-transitory computer-readable storage medium including instructions, which when executed, cause at least one processor to evaluate blood flow in a vessel of a patient, by carrying out steps that include:
- receive pressure data measured in the vessel, the pressure data including:
  - a first series of pressure measurements from a first pressure sensor positioned on a first side of a stenosis within a vessel;
  - a second series of pressure measurements from a second pressure sensor positioned on a second side of the stenosis within the vessel;
- calculate a stability index for each of two or more portions of the pressure data, wherein the stability index for each of two or more portions of the pressure data indicates at least one of heart rate stability and catheter stability for the respective portion of the pressure data;
- identify, based on the stability index for each of two or more portions of the pressure data, an optimal time window within the pressure data for calculating fractional flow reserve (FFR);
- calculate an FFR value based on the pressure data in the optimal time window;
- administer a treatment to the patient when the FFR value is less than a threshold FFR value;
- wherein the FFR calculation module is further configured to calculate a catheter instability indicator based on an amount of high frequency noise and baseline drift present in the pressure data and wherein the stability index for each of two or more portions of the pressure data is based on the catheter instability indicator.

* * * * *